United States Patent [19]

Brown

[11] Patent Number: 5,990,177
[45] Date of Patent: Nov. 23, 1999

[54] TREATMENT OF DISEASES MEDIATED BY THE NITRIC OXIDE/CGMP/PROTEIN KINASE G PATHWAY

[75] Inventor: David A. Brown, Ellicott City, Md.

[73] Assignee: Codon Pharmaceuticals, Inc., Gaithersburg, Md.

[21] Appl. No.: 08/933,144

[22] Filed: Sep. 18, 1997

Related U.S. Application Data

[60] Provisional application No. 60/026,577, Sep. 18, 1996, provisional application No. 60/035,947, Jan. 21, 1997, provisional application No. 60/036,863, Feb. 4, 1997, and provisional application No. 60/048,597, Jun. 4, 1997.

[51] Int. Cl.$^6$ ................................................ A61K 31/045
[52] U.S. Cl. ........................ 514/729; 514/724; 514/739
[58] Field of Search .................................... 514/724, 729, 514/739

[56] References Cited

U.S. PATENT DOCUMENTS 5,747,532   5/1998   Lai ........................................... 514/305

OTHER PUBLICATIONS

Merck Index, 10th Edn, # 1708, 2696, 3744, 7756, 9522, 1983.

*Primary Examiner*—James H. Reamer
*Attorney, Agent, or Firm*—John E. Tarcza; Glenn E. Karta

[57] ABSTRACT

Disclosed are methods and compositions for stimulating cellular nitric oxide (NO) synthesis, cyclic guanosine monophosphate levels (cGMP), and protein kinase G (PKG) activity for purposes of treating diseases mediated by deficiencies in the NO/cGMP/PKG signal transduction pathway, by administration of various compounds including alcohols, diols and/or triols and their analogues.

20 Claims, No Drawings

TREATMENT OF DISEASES MEDIATED BY THE NITRIC OXIDE/CGMP/PROTEIN KINASE G PATHWAY

CROSS REFERENCE TO RELATED APPLICATIONS

This application is a continuation-in-part of provisional application Ser. No. 60/026,577 filed Sep. 18, 1996, of provisional application Ser. No. 60/035,947 filed Jan. 21, 1997, of provisional application Ser. No. 60/036,863 filed Feb. 4, 1997, and of provisional application Ser. No. 60/048,597 filed Jun. 4, 1997.

STATEMENT REGARDING FEDERALLY SPONSORED RESEARCH OR DEVELOPMENT

Not Applicable

BACKGROUND OF THE INVENTION

1. Field of the Invention

The present invention relates to stimulating cellular nitric oxide (NO) synthesis, cyclic guanosine monophosphate levels (cGMP), and protein kinase G (PKG) activity for purposes of treating diseases mediated by deficiencies in the NO/cGMP/PKG signal transduction pathway, by administration of various compounds including alcohols, diols and/or triols and their analogues.

2. Description of Related Art

The compositions which are the subject of the present invention have been found to increase the melanin content of mammalian melanocytes, increase pigmentation in the epidermis of a mammal, and treat or prevent various skin and proliferative disorders. See U.S. application Ser. No. 60/026,577 filed Sep. 18, 1996; application Ser. No. 60/035,947 filed Jan. 21, 1997; application Ser. No. 60/036,863 filed Feb. 4, 1997, and application Ser. No. 60/048,597 filed Jun. 4, 1997. It has now been found that the present compositions may be used for treating diseases mediated by deficiencies in the NO/cGMP/PKG signal transduction pathway.

SUMMARY OF THE INVENTION

In one aspect, the present invention provides a method for stimulating cellular synthesis of nitric oxide (NO), which comprises administering to mammalian cells in need of such stimulation an effective amount of a compound having the structure:

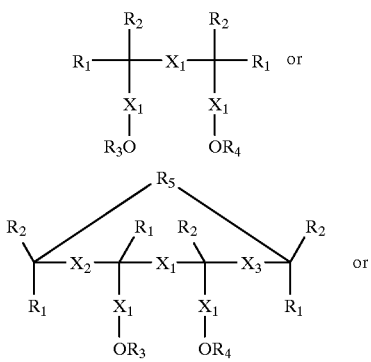

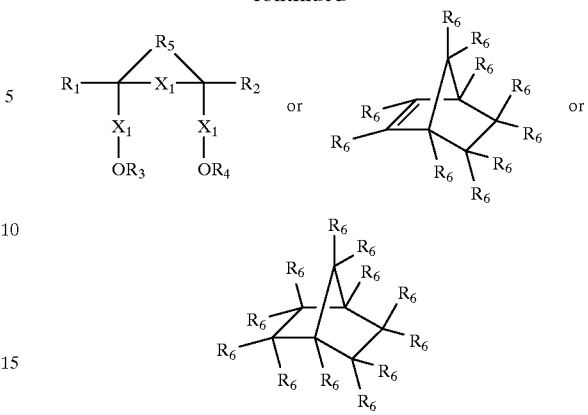

wherein
$X_1$, $X_2$, and $X_3$ are independently selected from a single bond; or a group containing from one atom to twenty atoms, at least one of which is carbon, nitrogen, oxygen or sulfur;

each of $R_1$ and $R_2$ is independently selected from hydrogen; halogen; or a group containing from one atom to twenty atoms, one of which is carbon, nitrogen, oxygen, or sulfur;

each of $R_3$ and $R_4$ is independently selected from hydrogen or an acyl or amino acyl group containing from one atom to twenty atoms, at least one of which is carbon, nitrogen, oxygen, or sulfur;

$R_5$ is a linear, branched or unbranched, cyclic, bicyclic or polycyclic group containing from one atom to fifty atoms, at least one of which is carbon, nitrogen, oxygen, or sulfur, and each $R_6$ is independently selected from hydrogen; halogen; or a group containing from one atom to twenty atoms, one of which is carbon, nitrogen, oxygen, or sulfur; hydroxyl, hydroxymethyl, —$(CH_2)_n$OH, —$(CH_2)_n$O$R_1$, —$(CH_2)_n$—CH(OH)—CHOH, —$(CH_2)_n$—CH(OH)—CH(OH)$R_1$, —$(CH_2)_n$—CH(OH)—$(CH_2)_n$—CH$_2$(OH), —$(CH_2)_n$—CH(OH)—$(CH_2)_n$—CH(OH)$R_1$ or —$CH_2OR_3$, wherein each n is independently an integer from 0–25;

and pharmaceutically acceptable salts thereof.

In another aspect, the present invention provides a composition for stimulating cellular synthesis of nitric oxide (NO), which comprises:
a) an effective amount of one or more compounds described above; and
b) a suitable carrier.

DETAILED DESCRIPTION OF THE INVENTION

The present invention is based on the discovery of a class of compounds whose action is blocked by scavengers of nitric oxide (NO), and by inhibitors of cyclic guanosine monophosphate (cGMP) or inhibitors of cGMP-activated protein kinase (PKG). This indicates that these compounds act via the NO/cGMP/PKG signal transduction pathway. Unlike previous compounds like nitroglycerin and isosorbide dinitrate that stimulate this pathway by releasing NO upon reaction with intracellular sulfhydryl groups (Smith and Reynard, 1992, Pharmacology, W.B. Saunders Co., Philadelphia, Pa., pp. 626–31), the compounds of this invention appear to act by direct stimulation of nitric oxide synthase (NOS) activity, thus generating NO de novo. Whereas depletion of intracellular sulfhydryl groups rapidly leads to tolerance and ineffectiveness of nitroglycerin and related compounds (Smith and Reynard, 1992), tolerance will not be acquired to the compounds of the present invention since they do not require the presence of sulfhydryl groups for generation. Thus, it is contemplated that the compounds of the present invention will provide a preferred alternative method of treatment for conditions presently treated by NO donors.

Both clinical application and research studies have demonstrated that stimulation of the NO/cGMP/PKG pathway is useful for treatment of:

(i) heart disease including stable angina pectoris, unstable angina, myocardial infarction, and myocardial failure associated with myocardial ischemia, atherosclerosis, vascular hypertrophy, and thrombosis (Cooe and Dzau, 1997, *Annu. Rev. Med.* 48:489–509; Thadani, 1997, *Cardiovasc. Drugs* 10:735);

(ii) hypertension (Cooe and Dzau, 1997);

(iii) stroke (Samdani, et al., 1997, Stroke 28:1283–1288);

(iv) primary pulmonary hypertension, chronic obstructive pulmonary disease, and adult respiratory distress syndrome (Adnot and Raffestin, 1996, *Thorax* 51:762–764; Marriott and Higenbottam, 1997, *Schweiz Med. Wochenschr.* 127:709–714);

(v) microvascular functional abnormalities in diabetes that link insulin-resistance to hypertension, thrombosis and atherosclerosis (Tooke, et al., 1996, *Diabetes Res. Clin. Pract.* 31Suppl:S127–S132; Baron, 1996, *J. Investig. Med.* 44:406–412);

(vi) hemostatic irregularities of glomerular vascular and tubular function with consequences for development of hypertension (Kone and Baylis, 1997, *Am. J. Physiol.* 10:F561–578; *Am. J. Hypertens.* 10:129–140);

(vii) microvascular irregularities in the liver with consequences for biliary transport and tissue regeneration (Suematsu, et al., 1996, *Cardiovasc. Res.* 32:679–686);

(viii) disorders of bladder function and reflex relaxation for micturition (Andersson, 1996, *Curr. Opin. Obstet. Gynecol.* 8:361–365);

(ix) disorders of neurotransmitter release, neuron morphogenesis, synaptic plasticity, and neuroendocrine regulation (Dawson and Dawson, 1996, *Neurochem. Int.* 29:97–110; Brann, et al., 1997, *Neuroendocrinology* 65:385–395);

(x) regional pain including migraine headaches (Mashimo, et al., 1997, *J. Clin. Pharmacol.* 37:330–335; Packard and Ham, 1997, Mar. 37:142–152);

(xi) gastrointestinal protection from non-steroidal anti-inflammatory drugs (Rishi, et al., 1996, *Indian J. Physiol. Pharmacol.* 40:377–379);

(xii) benign anal disease (Gorfine, 1995, *Dis. Colon Rectum* 38:453–456);

(xiii) impotence (Andersson and Stief, 1997, *World J. Urol.* 15:14–20);

(xiv) regulation of tissue free radical injury (Rubbo, et al., 1996, *Chem. Res. Toxicol.* 9:809–820); and (xv) inhibition of tumor growth, tumor apoptosis, angiogenesis, and metastasis (Pipili-Synetos, et al., 1995, *Br. J. Pharmacol.* 116:1829–1834; Xie, et al., 1996, *J. Leukoc. Biol.* 59:797–803); and (xvi) stimulation of wound healing including cuts, tendon injury and thermal injury (Schaffer, et al., 1996, *J. Surg. Res.* 63:237–240; Murrell, et al., 1997, *Inflamm. Res.* 46:19–27; Carter, et al., 1994, *Biochem. J.* 304(Pt 1):201–04).

In addition, the NO/cGMP/PKG pathway mediates melanogenesis induced by ultraviolet light (Romero-Graillet, et al., 1996, *J. Biol. Chem.* 271:28052–28056; Romero-Graillet, et al., 1997, *J. Clin. Invest.* 99:635–642) and aliphatic and alicyclic diols (United States patent application Ser. No. 08/933/143, entitled "Dermatalogical Compositions and Methods" filed concurrently herewith).

The active compounds according to the present invention have the structures described above. More preferably, each X is independently selected from a single bond; or $C_1$–$C_{10}$ alkylene, $C_2$–$C_{10}$ alkenylene, or $C_2$–$C_{10}$ alkynylene, each of which may contain one or more different heteroatoms or heteroatoms of the same type. More preferably each of $R_1$ and $R_2$ is independently selected from hydrogen; fluoro; chloro; or $C_1$–$C_{20}$ alkyl, $C_2$–$C_{20}$ alkenyl, $C_2$–$C_{20}$ alkynyl, $C_7$–$C_{20}$ aralkyl, $C_8$–$C_{20}$ aralkenyl, $C_8$–$C_{20}$ aralkinyl, or $C_6$–$C_{20}$ aryl, each of which may contain one or more different heteroatoms or heteroatoms of the same type, or carboxyl, carboxamido, carbalkoxy, sulfamido, sulfonamido; hydroxyl, or amino. More preferably each of $R_3$ or $R_4$ is independently selected from hydrogen or $C_1$–$C_{18}$ acyl, which may contain one or more different heteroatoms or heteroatoms of the same type. More preferably $R_5$ contains from two to twenty carbon atoms, each may contain one or more different heteroatoms or heteroatoms of the same type.

The preparation of the present compounds would be apparent to one of ordinary skill, and many of them are commercially available. Representative preferred compounds include, but are not limited to:

1,2-Ethanediol
1,2-Propanediol (Propylene Glycol)
(S)-(+)-1,2-Propanediol [(S)-(+)-1,2-Propylene Glycol]
1,3-Propanediol
2,3-Dimethyl-2,3-Butanediol
2,3-Dimethyl-1,2-Butanediol
1-Phenyl-1,2-Propanediol
2-Methyl-1,3-Propanediol
1,2-Butanediol
1,3-Butanediol
1,4-Butanediol
2,3-Butanediol
(2R,3R)-(−)-2,3-Butanediol
(2S,3S)-(+)-2,3-Butanediol
2,3-meso-Butanediol
1,2-Pentanediol
1,4-Pentanediol
1,5-Pentanediol
2,4-Pentanediol
1,2-cis-cyclopentanediol
1,2-trans-cyclopentanediol
1,2-cis-cyclohexaneanediol
1,2-trans-cyclohexanediol
1,2-dihydroxy-4,5-cyclohexanediol carbonate
1,2,4,5-tetrahydroxycyclohexane
1,2-Hexanediol
1,5-Hexanediol
1,6-Hexanediol 2,5-Hexanediol
1,2-Heptanediol
1,7-Heptanediol
7-Octene-1,2-diol
1,2-Octanediol
1,8-Octanediol
1,2-Nonanediol
1,9-Nonanediol
1,2-Decanediol
1,10-Decanediol
1,2-Dodecanediol
1,12-Dodecanediol
1,2-Tetradecanediol
1,14-Tetradecanediol
1,2-Hexadecanediol
1,16-Hexadecanediol
Glycerol
1,2,4-Butanetriol
1,2,3-Trihydroxyhexane
1,2,6-Trihydroxyhexane
1,2,3-Heptanetriol
β-estradiol
azabicyclo-(2,2,1)-heptanediol-3-one
1,4-dioxane-2,3-diol
5-norbornene-2,2-dimethanol
norbornane-2,2-dimethanol
2,3-norbornanediol (exo or endo or cis or trans)
2,3-cis-exo-norbornanediol
α-norborneol
2-norbornanemethanol
norbornane
borneol
camphor
camphene
camphane
norbornane acetic acid
norbornane-carboxylic acid
norbornane-dicarboxylic acid
2-endo-hexadecylamino-5-norbornene-2-exo-methanol
2-endo-hexadecylamino-5-norbornene-2,3-exo-dimethanol
2-(propyl-1,2-diol)-norbornane
1,2-dithiane-trans-4,5-diol
2,3-pyridinediol
2,3-pyridinediol hydrogen chloride
2,3-pyridinediol glycolic acid
2,3-dipyridyl-2,3-butanediol
2,2,4,4-tetramethyl-1,3-cyclobutanediol Particularly preferred compounds of this invention are 5-norbornene-2,2-dimethanol; norbornane-2,2-dimethanol; 2-norbornanemethanol; 1,2-cis-cyclopentanediol; 2,3-cis-exo-norbornanediol, 2-(propyl-1,2-diol)-norbornane and 3,3-dimethyl-1,2-butanediol. Other preferred compounds are 1,2-trans-cyclopentanediol; 2,3-dimethyl-2,3-butanediol; 2-methyl-1,3-propanediol; 2,3-butanediol; and propylene glycol.

The methods and compositions of the present invention contemplate the use of one or more of the above-mentioned compounds as an active ingredient to stimulate nitric oxide synthase (NOS) activity, resulting in generation of nitric oxide (NO), generation of cyclic guanosine monophosphate (cGMP), and activation of cGMP-activated protein kinase (PKG) activity. This should affect a variety of physiological processes depending upon the treated tissue, including but not limited to mediation of blood vessel relaxation, mediation of neurotransmission, mediation of neuronal differentiation, regulation of free-radical injury, and mediation of melanogenesis. In a preferred embodiment, the active ingredient(s) is given orally, intravenously, or transdermally in an acceptable formulation. Depending on the specific application, the compositions of the present invention may also include other active ingredients, as well as inert or inactive ingredients.

The methods and compositions of the present invention contemplate the use of one or more of the above-mentioned compounds as an active ingredient. In a preferred embodiment, the active ingredient(s) is given orally, intravenously, or transdermally in an acceptable formulation. A particularly preferred carrier for some formulations is 1,2-propylene glycol since it is an excellent solvent for certain compounds in this invention including but not limited to 5-norbornene-2,2-dimethanol, 5-norbornane-2,2-dimethanol and 3,3-dimethyl-1,2-butanediol. Additionally, 1,2-propylene glycol as carrier has itself, as described in this invention, similar but lessor activity than the preferred active ingredient(s). Depending on the specific application, the compositions of the present invention may also include other active ingredients, as well as inert or inactive ingredients.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies and repetition rates. In general, it is contemplated that unit dosage form compositions according to the present invention will contain from about 0.01 mg to about 100 mg of active ingredient, preferably about 0.1 mg to about 10 mg of active ingredient. Topical formulations (such as creams, lotions, solutions, etc.) may have a concentration of active ingredient of from about 0.01% to about 50%, preferably from about 0.1% to about 10%.

The use of and useful and novel features of the present methods and compositions will be further understood in view of the following non-limiting examples.

EXAMPLE 1

Cloudman S91 mouse melanoma cells were obtained from ATCC and cultured in MEM (BioWhittaker) with 10% calf serum (BioWhittaker or Hyclone). Cells were plated at $10^5$ cells/well in 6-well plates the day before treatments, in media containing 10% calf serum. Media was changed to MEM with 2% calf serum concomitant with addition of treatments (Eller, et al., 1996, *Proc. Natl. Acad. Sci.* 93:1087–1092). Six days later, media was removed and S91 cells were washed twice with 2 ml 1XPBS (BioWhittaker), 1 ml of 0.05% trypsin/EDTA (BioWhittaker) was added, and cells were incubated at 37° C. until detached from plastic dishes. Four ml of media containing 10% calf serum was added, cells were mixed by pipette action until no clumps of cells remained, and 0.5 ml were counted on a Coulter counter.

Tyrosinase was analyzed using previously described procedures (Pomerantz, 1966, *J. Biol. Chem.* 241:161–168). Cells were solubilized by sonicating for 5 seconds in 600 ul 50 mM phosphate buffer pH 6.8 containing 0.5% Triton-X100, followed by vortexing, incubation on ice for 30 minutes, and then revortexing. From this, 200 ul aliquots were combined with 200 ul of reaction mixture containing either 75 uM tyrosine, 75 uM L-Dopa, and 2 uCi L-[3,5-$^3$H]Tyrosine in 50 mM NaPO$_4$ pH 6.8 (L-Dopa +), or, 75 uM tyrosine, and 2 uCi L-[3,5-$^3$H]Tyrosine in 50 mN NaPO$_4$ pH 6.8 (L-Dopa −), and then incubated 1 hr at 37° C. Reactions were stopped by addition of 400 ul 10% activated charcoal in 0.1N HCl and incubation on ice for 15 min. This mixture was centrifuged at 17,300×g for 5 min, and 400 ul supernatant was then filtered through a 0.22 uM GV Durapore centrifugal filter unit (Millipore) by centrifuging at 17,300×g for 5 min. Filtrate was added to 4 ml Fisher Plus scintillation fluid and counted on a Hewlett Packard 2000A scintillation counter. Tyrosinase activity was calculated as dpm/$10^3$ cells. Each sample was analyzed with and without L-Dopa, a necessary cofactor for tyrosinase (Pomerantz, 1966). All reported tyrosinase values are exclusive of counts that occurred in buffer blanks and L-dopa negative aliquots.

It has been previously demonstrated that a variety of aliphatic and alicyclic diols including 5-norbornene-2,2-dimethanol (5-NBene-2,2-DM) induce melanogenesis in S91 cells. The results presented in Table 1 show that induction of tyrosinase (the rate-limiting enzyme in melanogenesis) by 5-NBene-2,2-DM is not blocked by highly specific inhibitors of the PKC and PKA pathways. In fact, treatment of S91 cells with either the highly specific PKA inhibitor H-89 (Chijiwa, et al., 1990, *J. Biol. Chem.* 265:5267–5272), or the highly specific PKC inhibitor GF109203X (Toullec, et al., 1991, *J. Biol. Chem.* 266:15771–15781) resulted in augmentation of basal and 5-NBene-2,2-DM-induced tyrosinase levels (Table 1). Thus, 5-NBene-2,2-DM does not appear to act via either the PKC or PKA pathways.

In contrast, both the nitric oxide (NO) scavenger PTIO (2-phenyl-4,4,5,5-tetramethylimidazoline-1-oxyl-3-oxide), the cyclic guanosine monophosphate (cGMP) inhibitor LY83583 (6-anilino-5,8-quinolinequinone), and the PKG (cGMP-activated protein kinase) inhibitor KT5823 reduced induction of melanogenesis by 5-NBene-2,2-DM in S91 cells (Table 2). These results demonstrate that induction of melanogenesis by 5-NBene-2,2-DM occurs by the NO/cGMP/PKG pathway.

Previously, it has been demonstrated that NO donors can stimulate melanogenesis in normal human melanocytes (Romero-Graillet, et al., 1996, *J. Biol. Chem.* 271). Results presented here demonstrate that 5-NBene-2,2-DM can stimulate melanogenesis with a potency equivalent or greater than that of NO donors, even though 5-NBene-2,2-DM has no ability to donate NO. Since induction of melanogenesis by 5-NBene-2,2-DM occurs by the NO/cGMP/PKG pathway, 5-NBene-2,2-DM must directly stimulate NO synthesis.

These results demonstrate that stimulation of NO synthesis and the cGMP/PKG pathway by 5-NBene-2,2-DM provides an efficient alternative to stimulation of this pathway by NO donors. Thus, 5-NBene-2,2-DM and related compounds described in this invention will serve as alternative therapeutics for treatment of a variety of diseases mediated by perturbations of the NO/cGMP/PKG pathway.

TABLE 1

PKA/PKC Inhibitors

|  | dpm/hr/ $10^3$ cells | % of 5-NBene-DM Induction |
| --- | --- | --- |
| 5 mM 5-NBene-2,2-DM (n = 2) | 2142 ± 185[1] | 100% |
| 5 mM 5-NBene-2,2-DM/1 uM H-89[2] (n = 1) | 3255 | 152% |
| 5 mM 5-NBene-2,2-DM/10 uM H-89 (n = 1) | 2428 | 113% |
| 5 mM 5-NBene-2,2-DM/ 0.1 uM GF109203X[3] (n = 1) | 2700 | 126% |
| 5 mM 5-NBene-2,2-DM/ 1.0 uM GF109203X (n = 1) | 5055 | 236% |

|  | dpm/hr/ $10^3$ cells | % of Control |
| --- | --- | --- |
| Untreated Control (n = 2) | 128 ± 4 | 100% |
| 1 uM H-89[2] (n = 1) | 177 | 138% |
| 10 uM H-89 (n = 1) | 765 | 598% |
| 0.1 uM GF109203X[3] (n = 1) | 270 | 211% |
| 1.0 uM GF109203X (n = 1) | 650 | 508% |

[1]X ± SE
[2]H-89: PKA inhibitor
[3]GF109203X: PKC inhibitor

TABLE 2

|  | dpm/hr/ $10^3$ cells | % of 5-NBene-2,2-DM Induction |
| --- | --- | --- |
| NO/PKG Inhibitors - Experiment 1 | | |
| 5 mM 5-NBene-2,2-DM (n = 4) | 5018 ± 415[1] | 100% |
| 5 mM 5-NBene-2,2-DM/ 20 uM PTIO[4] (n = 2) | 3703 ± 262 | 74% |
| 5 mM 5-NBene-2,2-DM/ 0.5 uM KT5823[5] (n = 2) | 1528 ± 190 | 31% |
| NO/PKG Inhibitors - Experiment 2 | | |
| 5 mM 5-NBene-2,2-DM (n = 4) | 5640 ± 323 | 100% |
| 5 mM 5-NBene-2,2-DM/ 20 uM PTIO[4] (n = 2) | 4078 ± 429 | 72% |
| 5 mM 5-NBene-2,2-DM/ 40 uM PTIO (n = 2) | 3351 ± 994 | 59% |
| 5 mM 5-NBene-2,2-DM/ 0.5 uM KT5823[5] (n = 2) | 2940 ± 261 | 52% |
| 5 mM 5-NBene-2,2-DM/ 1.0 uM KT5823 (n = 2) | 1688 ± 324 | 30% |
| cGMP Inhibitor - Experiment 3 | | |
| 5 mM 5-NBene-2,2-DM (n = 4) | 6388 ± 460[1] | 100% |
| 5 mM 5-NBene-2,2-DM/ 0.1 uM LY83583[6] (n = 2) | 1389 ± 64 | 22% |
| 5 mM 5-NBene-2,2-DM/ 0.2 uM LY83583 (n = 2) | 300 ± 84 | 5% |

[1]X ± SE
[4]PTIO: Nitric oxide scavenger
[5]KT5823: PKG inhibitor
[6]LY85583: cGMP inhibitor

I claim:

1. A method for stimulating cellular synthesis of nitric oxide (NO) to a statistically significant level above background, which comprises administering to mammalian cells in need of such stimulation a pharmaceutical composition comprising an effective amount of a compound having the following structure:

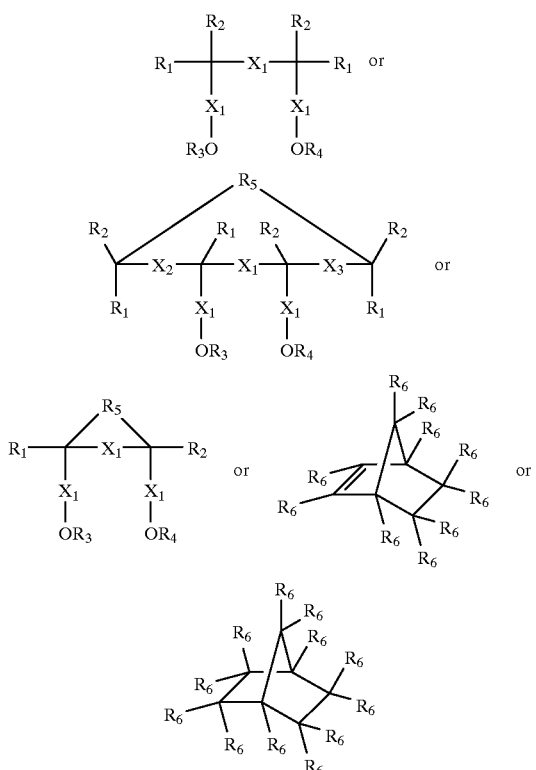

wherein

X₁, X₂ and X₃ are independently selected from a single bond; or a group containing from one atom to twenty atoms, at least one of which is carbon, nitrogen, oxygen or sulfur;

each of R₁, and R₂, is independently selected from hydrogen; halogen; or a group containing from one atom to twenty atoms, one of which is carbon, nitrogen, oxygen or sulfur;

each of R₃, and R₄, is independently selected from hydrogen or an acyl or amino acyl group containing from one atom to twenty atoms, at least one of which is carbon, nitrogen, oxygen or sulfur;

R₅ is a linear, branched, cyclic, bicyclic or polycyclic group containing from one atom to fifty atoms, at least one of which is carbon, nitrogen, oxygen, or sulfur, and each R₆ is independently selected from hydrogen; halogen; or a group containing from one atom to twenty atoms, one of which is carbon, nitrogen, oxygen, or sulfur; hydroxyl, hydroxymethyl, —(CH₂)ₙOH, —(CH₂)ₙOR₁, —(CH₂)ₙ—CH(OH)—CHOH, —(CH₂)ₙ—CH(OH)—CH(OH)R₁, —(CH₂)ₙ—CH (OH)—(CH₂)ₙ—CH₂(OH), —(CH₂)ₙ—CH(OH)—(CH₂)ₙ—CH(OH)R₁, or —CH₂OR₃ wherein each n is independently an integer from 0–25;

or pharmaceutically acceptable salts thereof, and a pharmaceutically suitable carrier.

2. The method of claim 1, wherein the compound is selected from the group consisting of 1,2-Ethanediol, 1,2-Propanediol (Propylene Glycol), (S)-(+)-1,2-Propanediol [(S)-(+)-1,2-Propylene Glycol], 1,3-Propanediol, 2,3-Dimethyl-2,3-Butanediol, 2,3-Dimethyl-1,2-Butanediol, 1-Phenyl-1,2-Propanediol, 2-Methyl-1,3-Propanediol, 1,2-Butanediol, 1,3-Butanediol, 1,4-Butanediol, 2,3-Butanediol, (2R,3R)-(−)-2,3-Butanediol, (2S,3S)-(+)-2,3-Butanediol, 2,3-meso-Butanediol, 1,2-Pentanediol, 1,4-Pentanediol, 1,5-Pentanediol, 2,4-Pentanediol, 1,2-cis-cyclopentanediol, 1,2-trans-cyclopentanediol, 1,2-cis-cyclohexaneanediol, 1,2-trans-cyclohexanediol, 1,2-dihydroxy-4,5-cyclohexanediol carbonate, 1,2,4,5-tetrahydroxycyclohexane, 1,2-Hexanediol, 1,5-Hexanediol, 1,6-Hexanediol, 2,5-Hexanediol, 1,2-Heptanediol, 1,7-Heptanediol, 7-Octene-1, 2-diol, 1,2-Octanediol, 1,8-Octanediol, 1,2-Nonanediol, 1,9-Nonanediol, 1,2-Decanediol, 1,10-Decanediol, 1,2-Dodecanediol, 1,12-Dodecanediol, 1,2-Tetradecanediol, 1,14-Tetradecanediol, 1,2-Hexadecanediol, 1,16-Hexadecanediol, Glycerol, 1,2,4-Butanetriol, 1,2,3-Trihydroxyhexane, 1,2,6-Trihydroxyhexane, 1,2,3-Heptanetriol, β-estradiol, azabicyclo-(2,2,1)-heptanediol-3-one, 1,4-dioxane-2,3-diol, 5-norbornene-2,2-dimethanol, norbornane-2,2-dimethanol, 2,3-norbornanediol (exo or endo or cis or trans), 2,3-cis-exo-norbornanediol, α-norborneol, 2-norbornanemethanol, norbornane, borneol, camphor, camphene, camphane, norbornane acetic acid, norbornane-carboxylic acid, norbornane-dicarboxylic acid, 2-endo-hexadecylamino-5-norbornene-2-exo-methanol, 2-endo-hexadecylamino-5-norbornene-2,3-exo-dimethanol, 2-(propyl-1,2-diol)-norbornane, 1,2-dithiane-trans-4,5-diol, 2,3-pyridinediol, 2,3-pyridinediol hydrogen chloride, 2,3-pyridinediol glycolic acid, 2,3-dipyridyl-2,3-butanediol, 2,2, 4,4-tetramethyl-1,3-cyclobutanediol.

3. The method of claim 2, wherein the compound is selected from 5-norbornene-2,2-dimethanol; norbornane-2, 2-dimethanol; 2-norbornanemethanol; 1,2-cis-cyclopentanediol; 2,3-cis-exo-norbornanediol, 2-(propyl-1, 2-diol)-norbornane and 3,3-dimethyl-1,2-butanediol.

4. The method of claim 1, wherein the stimulation of cellular synthesis of nitric oxide (NO) alleviates a condition selected from the group consisting of heart disease, hypertension, stroke, chronic obstructive pulmonary disease, adult respiratory distress syndrome, microvascular functional abnormalities in diabetes, hemostatic irregularities of glomerular vascular and tubular function, microvascular irregularities in the liver, disorders of bladder function and reflex relaxation for micturition, disorders of neurotransmitter release, neuron morphogenesis, synaptic plasticity, and neuroendrocrine regulation, migraine headaches, benign anal disease, and impotence.

5. The method of claim 1, wherein the stimulation of cellular synthesis of nitric oxide (NO) stimulates wound repair.

6. A pharmaceutical composition for stimulating cellular synthesis of nitric oxide (NO) to a statistically significant level above background, which comprises:

a) an effective amount of one or more compounds having the structure:

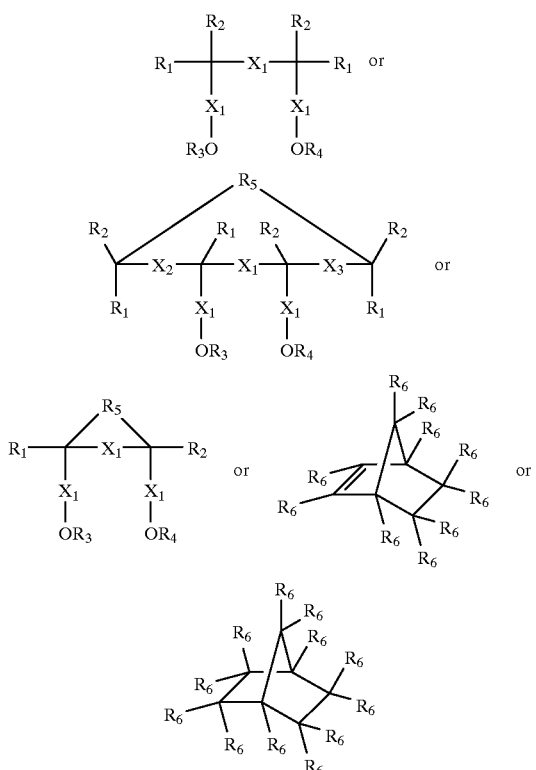

wherein

X₁, X₂ and X₃ are independently selected from a single bond; or a group containing from one atom to twenty atoms, at least one of which is carbon, nitrogen, oxygen or sulfur;

each of $R_1$, and $R_2$, is independently selected from hydrogen; halogen; or a group containing from one atom to twenty atoms, one of which is carbon, nitrogen, oxygen or sulfur;

each of $R_3$, and $R_4$, is independently selected from hydrogen or an acyl or amino acyl group containing from one atom to twenty atoms, at least one of which is carbon, nitrogen, oxygen or sulfur;

$R_5$ is a linear, branched, cyclic, bicyclic or polycyclic group containing from one atom to fifty atoms, at least one of which is carbon, nitrogen, oxygen, or sulfur, and each $R_6$ is independently selected from hydrogen; halogen; or a group containing from one atom to twenty atoms, one of which is carbon, nitrogen, oxygen, or sulfur; hydroxyl, hydroxymethyl, —$(CH_2)_n$OH, —$(CH_2)_n$OR$_1$, —$(CH_2)_n$—CH(OH)—CHOH, —$(CH_2)_n$—CH(OH)—CH(OH)R$_1$, —$(CH_2)_n$—CH(OH)—$(CH_2)_n$—CH$_2$(OH), —$(CH_2)_n$—CH(OH)—$(CH_2)_n$—CH(OH)R$_1$, or —CH$_2$OR$_3$ wherein each n is independently an integer from 0–25;

and pharmaceutically acceptable salts thereof; and b) a pharmaceutically suitable carrier.

7. The composition of claim 6, wherein the compound is selected from the group consisting of 1,2-Ethanediol, 1,2-Propanediol (Propylene Glycol), (S)-(+)-1,2-Propanediol [(S)-(+)-1,2-Propylene Glycol], 1,3-Propanediol, 2,3-Dimethyl-2,3-Butanediol, 2,3-Dimethyl-1,2-Butanediol, 1-Phenyl-1,2-Propanediol, 2-Methyl-1,3-Propanediol, 1,2-Butanediol, 1,3-Butanediol, 1,4-Butanediol, 2,3-Butanediol, (2R,3R)-(−)-2,3-Butanediol, (2S,3S)-(+)-2,3-Butanediol, 2,3-meso-Butanediol, 1,2-Pentanediol, 1,4-Pentanediol, 1,5-Pentanediol, 2,4-Pentanediol, 1,2-cis-cyclopentanediol, 1,2-trans-cyclopentanediol, 1,2-cis-cyclohexaneanediol, 1,2-trans-cyclohexanediol, 1,2-dihydroxy-4,5-cyclohexanediol carbonate, 1,2,4,5-tetrahydroxycyclohexane, 1,2-Hexanediol, 1,5-Hexanediol, 1,6-Hexanediol, 2,5-Hexanediol, 1,2-Heptanediol, 1,7-Heptanediol, 7-Octene-1,2-diol, 1,2-Octanediol, 1,8-Octanediol, 1,2-Nonanediol, 1,9-Nonanediol, 1,2-Decanediol, 1,10-Decanediol, 1,2-Dodecanediol, 1,12-Dodecanediol, 1,2-Tetradecanediol, 1,14-Tetradecanediol, 1,2-Hexadecanediol, 1,16-Hexadecanediol, Glycerol, 1,2,4-Butanetriol, 1,2,3-Trihydroxyhexane, 1,2,6-Trihydroxyhexane, 1,2,3-Heptanetriol, β-estradiol, azabicyclo-(2,2,1)-heptanediol-3-one, 1,4-dioxane-2,3-diol, 5-norbornene-2,2-dimethanol, norbornane-2,2-dimethanol, 2,3-norbornanediol (exo or endo or cis or trans), 2,3-cis-exo-norbornanediol, α-norborneol, 2-norbornanemethanol, norbornane, borneol, camphor, camphene, camphane, norbornane acetic acid, norbornane-carboxylic acid, norbornane-dicarboxylic acid, 2-endo-hexadecylamino-5-norbornene-2-exo-methanol, 2-endo-hexadecylamino-5-norbornene-2,3-exo-dimethanol, 2-(propyl-1,2-diol)-norbornane, 1,2-dithiane-trans-4,5-diol, 2,3-pyridinediol, 2,3-pyridinediol hydrogen chloride, 2,3-pyridinediol glycolic acid, 2,3-dipyridyl-2,3-butanediol, 2,2,4,4-tetramethyl-1,3-cyclobutanediol.

8. The composition of claim 7, wherein the compound is selected from 5-norbornene-2,2-dimethanol; norbornane-2,2-dimethanol; 2-norbornanemethanol; 1,2-cis-cyclopentanediol; 2,3-cis-exo-norbornanediol, 2-(propyl-1,2-diol)-norbornane and 3,3-dimethyl-1,2-butanediol.

9. The composition of claim 6, wherein the stimulation of cellular synthesis of nitric oxide (NO) alleviates a condition selected from the group consisting of heart disease, hypertension, stroke, chronic obstructive pulmonary disease, adult respiratory distress syndrome, microvascular functional abnormalities in diabetes, hemostatic irregularities of glomerular vascular and tubular function, microvascular irregularities in the liver, disorders of bladder function and reflex relaxation for micturition, disorders of neurotransmitter release, neuron morphogenesis, synaptic plasticity, and neuroendrocrine regulation, migraine headaches, benign anal disease, and impotence.

10. The composition of claim 6, wherein the stimulation of cellular synthesis of nitric oxide (NO) stimulates wound repair.

11. The method of claim 1 wherein the mammalian cells are a mammal.

12. The composition of claim 6 wherein the mammalian cells are a mammal.

13. The method of claim 1 wherein the stimulation of cellular synthesis of nitric oxide is not inhibited by Protein Kinase A or Protein Kinase C inhibitors but is inhibited by a Protein Kinase G inhibitor, a nitric oxide scavenger or a cGMP inhibitor.

14. The composition of claim 6 wherein the stimulation of cellular synthesis of nitric oxide is not inhibited by Protein Kinase A or Protein Kinase C inhibitors but is inhibited by a Protein Kinase G inhibitor, a nitric oxide scavenger or a cGMP inhibitor.

15. The method of claim 1 wherein the composition further comprises a Protein Kinase A inhibitor or a Protein Kinase C inhibitor.

16. The composition of claim 6 wherein the composition further comprises a Protein Kinase A inhibitor or a Protein Kinase C inhibitor.

17. The method of claim 1 wherein the compound is a bicyclic diol, a monocyclic diol or 3,3-dimethyl-1,2 butane diol.

18. The composition of claim 6 wherein the compound is a bicyclic diol, a monocyclic diol or 3,3-dimethyl-1,2 butane diol.

19. The method of claim 1 wherein the composition is in the form of a unitary dose.

20. The composition of claim 6 in the form of a unitary dose.

* * * * *